United States Patent
Dujovne et al.

(10) Patent No.: US 9,814,501 B2
(45) Date of Patent: Nov. 14, 2017

(54) CANNULATED TELESCOPIC FEMORAL NECK SCREW DEVICE AND RELATED FIXATION METHOD

(71) Applicant: PEGA MEDICAL INC., Laval, Quebec (CA)

(72) Inventors: Ariel Ricardo Dujovne, Cote St-Luc (CA); Francois Fassier, Outremont (CA); Marie Gdalevitch, Montreal (CA); Fady Rayes, Vaudreuil-Dorion (CA)

(73) Assignee: PEGA MEDICAL INC., Laval (CA)

( * ) Notice: Subject to any disclaimer, the term of this patent is extended or adjusted under 35 U.S.C. 154(b) by 0 days.

(21) Appl. No.: 14/762,926

(22) PCT Filed: Jan. 24, 2014

(86) PCT No.: PCT/CA2014/000053
§ 371 (c)(1),
(2) Date: Jul. 23, 2015

(87) PCT Pub. No.: WO2014/113879
PCT Pub. Date: Jul. 31, 2014

(65) Prior Publication Data
US 2015/0366591 A1 Dec. 24, 2015

Related U.S. Application Data

(63) Continuation of application No. 13/750,881, filed on Jan. 25, 2013, now abandoned.

(51) Int. Cl.
*A61B 17/74* (2006.01)
*A61B 17/86* (2006.01)

(52) U.S. Cl.
CPC ........ *A61B 17/742* (2013.01); *A61B 17/8685* (2013.01)

(58) Field of Classification Search
CPC ... A61B 17/74; A61B 17/742; A61B 17/8685; A61B 17/864; A61B 2017/681; A61B 17/7216; A61B 17/7225
See application file for complete search history.

(56) References Cited

U.S. PATENT DOCUMENTS

| 2,612,159 A | 9/1952 | Collison |
| 3,990,438 A * | 11/1976 | Pritchard ............... A61B 17/72 |
| | | 606/309 |

(Continued)

FOREIGN PATENT DOCUMENTS

| DE | WO 2004069065 A1 * | 8/2004 | ............ A61B 17/74 |
| WO | WO2004069065 | 8/2004 | |

OTHER PUBLICATIONS

International Search Report and Written Opinion for PCT/CA2014/000053.

(Continued)

*Primary Examiner* — Julianna N Harvey
(74) *Attorney, Agent, or Firm* — Damien Calvet; Brouillette Legal, Inc.

(57) ABSTRACT

A screw assembly and method developed for the fixation of femoral neck fractures without interruption of the growth process is disclosed. The screw assembly includes a male component that is attached to the lateral cortex and a female component that is attached at the proximal epiphysis. Anchorage of the components is achieved through screw-type fixation. The screw has a built-in feature that allows for free extension of its length as the fracture site or the slipped capital physeal plate heals and normal patient growth continues. Stable fixation and rotational stability are created at the fracture (slip) site while avoiding compression forces, thus avoiding premature closure of the physeal plate.

16 Claims, 14 Drawing Sheets

(56) References Cited

U.S. PATENT DOCUMENTS

| | | | |
|---|---|---|---|
| 4,640,271 A | | 2/1987 | Lower |
| 4,657,001 A | * | 4/1987 | Fixel ................. A61B 17/74 606/66 |
| 4,940,467 A | * | 7/1990 | Tronzo ............... A61B 17/742 606/304 |
| RE33,348 E | * | 9/1990 | Lower ................ A61B 17/8685 606/304 |
| 5,827,285 A | * | 10/1998 | Bramlet ............... A61B 17/68 411/166 |
| 6,007,337 A | | 12/1999 | Bauer |
| 6,302,887 B1 | | 10/2001 | Spranza et al. |
| 2004/0260288 A1 | | 12/2004 | Means, Jr. |
| 2006/0264954 A1 | * | 11/2006 | Sweeney, II ....... A61B 17/8685 606/312 |
| 2008/0188899 A1 | | 8/2008 | Bottlang et al. |
| 2009/0157123 A1 | * | 6/2009 | Appenzeller ......... A61B 17/68 606/301 |
| 2009/0287214 A1 | * | 11/2009 | Yu ..................... A61B 17/74 606/64 |
| 2010/0036440 A1 | * | 2/2010 | Morris ................ A61B 17/72 606/320 |
| 2010/0211112 A1 | * | 8/2010 | Kuster ............... A61B 17/746 606/290 |
| 2011/0106172 A1 | * | 5/2011 | Wallenstein ....... A61B 17/8605 606/286 |
| 2011/0313473 A1 | | 12/2011 | Prandi et al. |
| 2012/0184993 A1 | * | 7/2012 | Arambula .......... A61B 17/7064 606/246 |

OTHER PUBLICATIONS

"Biomechanical analysis of screw fixation vs. K-wire fixation of a slipped capital femoral epiphysis model", Claudia Druschel et al., Biomed Tech 2012; 57:157-162.

* cited by examiner

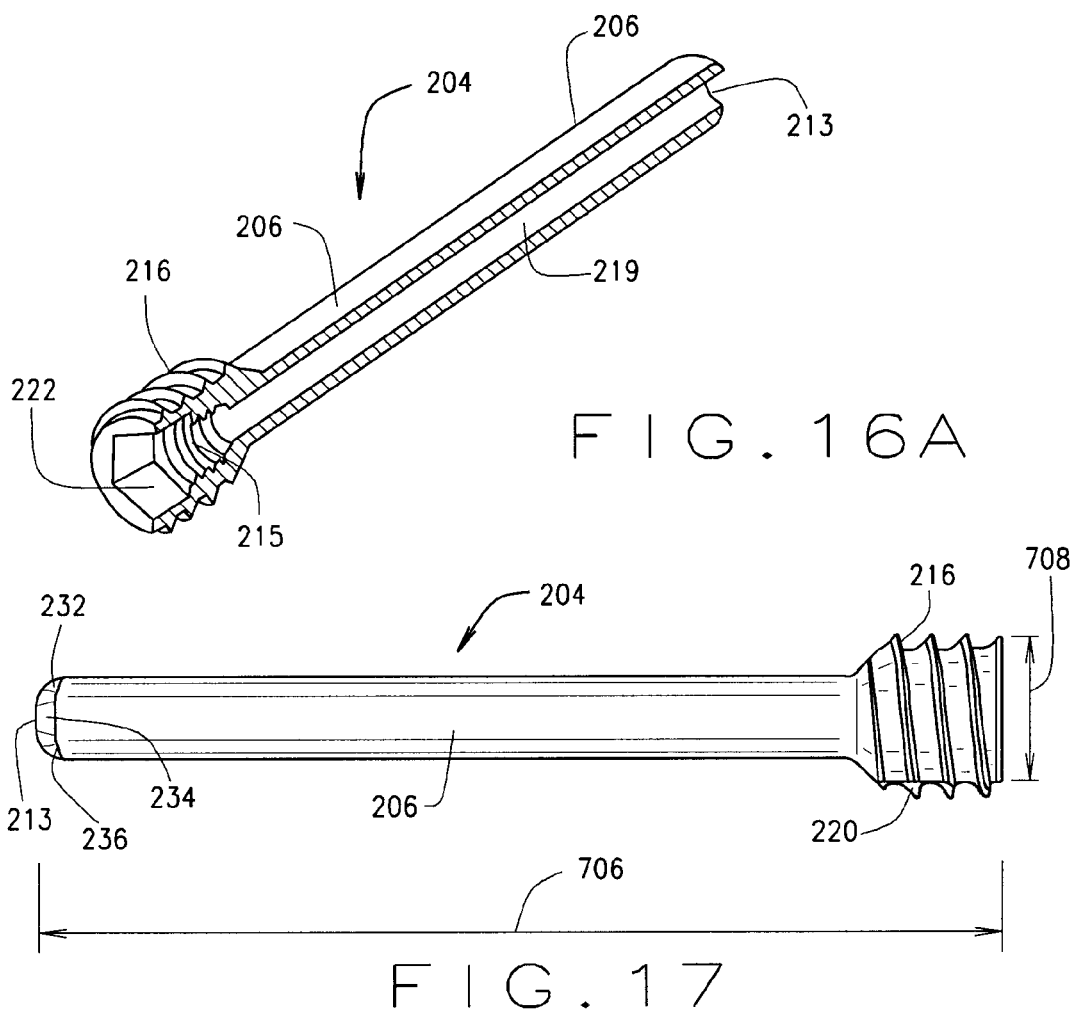
FIG. 16A
FIG. 17
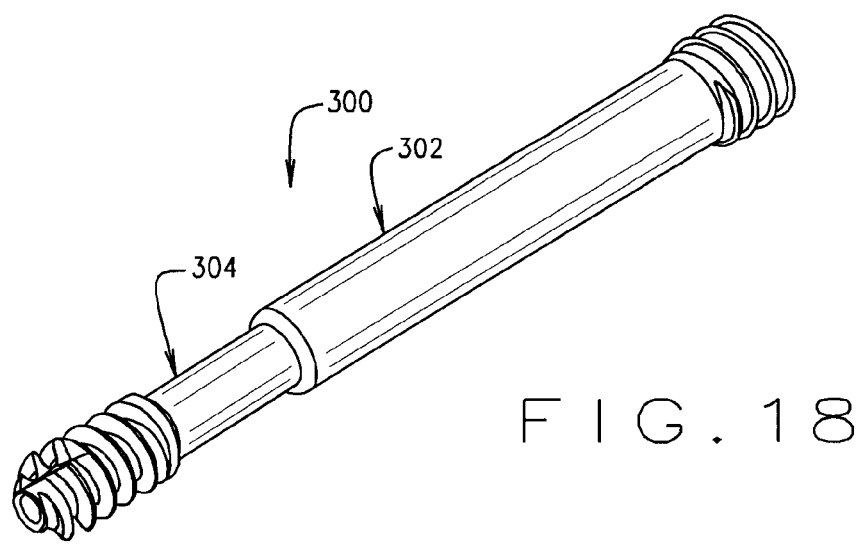
FIG. 18

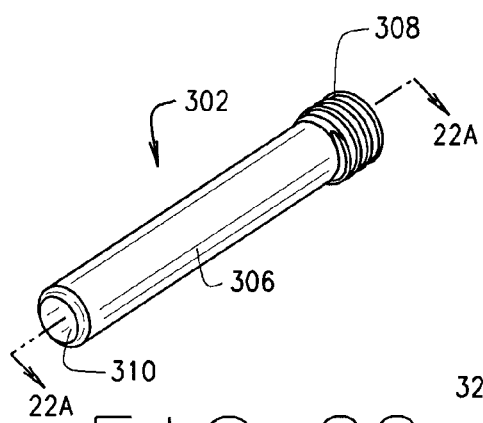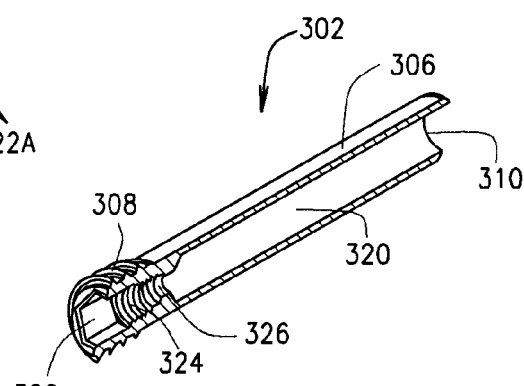
FIG. 22    FIG. 22A
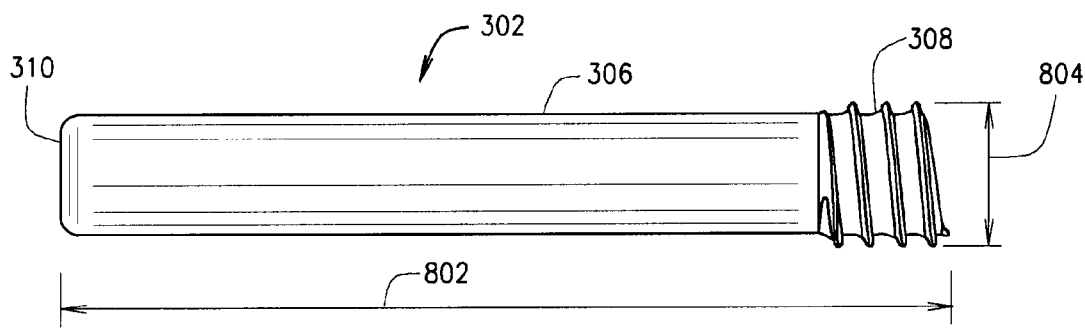
FIG. 23
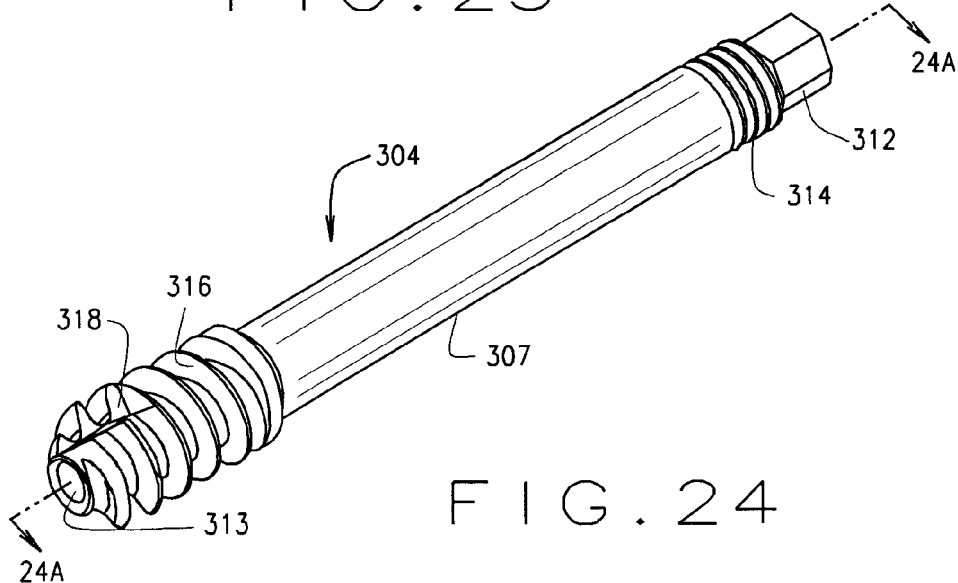
FIG. 24

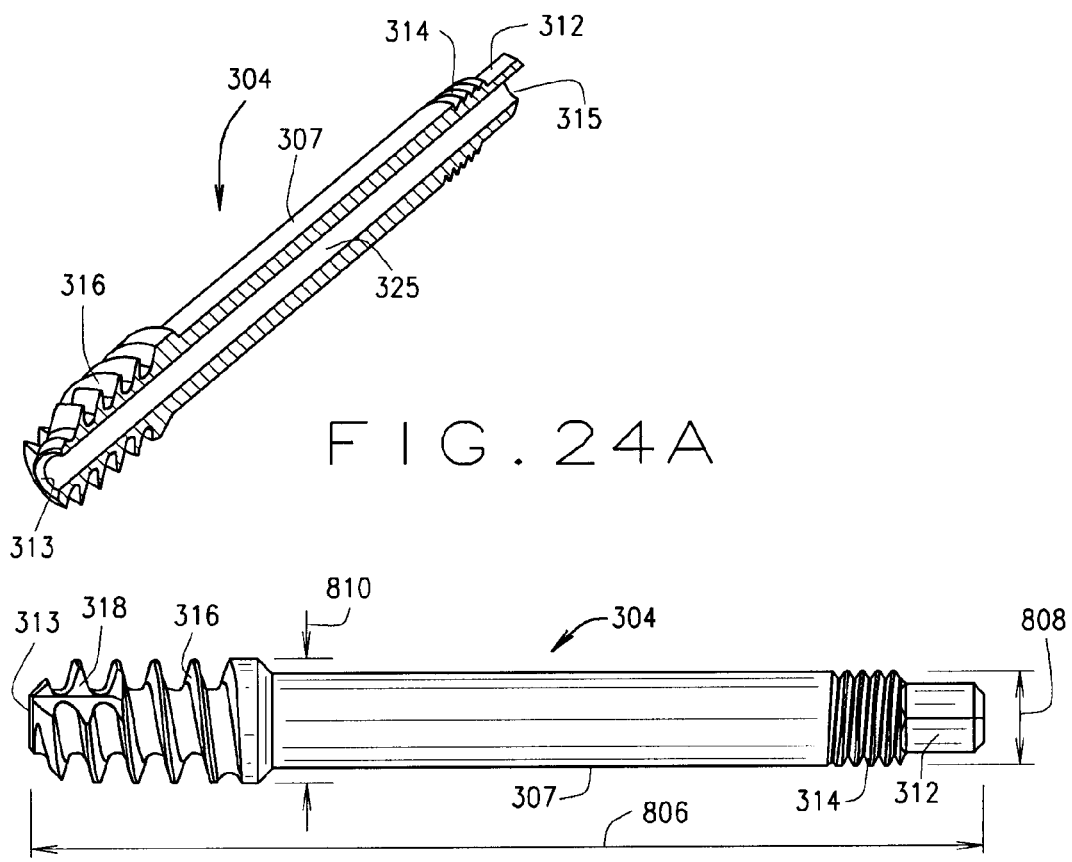
FIG. 24A
FIG. 25
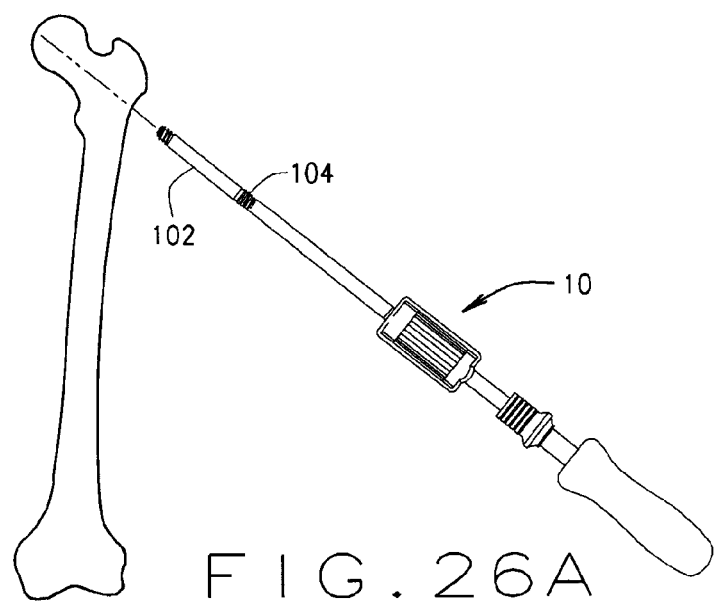
FIG. 26A

CANNULATED TELESCOPIC FEMORAL NECK SCREW DEVICE AND RELATED FIXATION METHOD

CROSS-REFERENCE TO RELATED APPLICATIONS

The present patent application claims the benefits of priority of U.S. patent application Ser. No. 13/750,881, entitled "CANNULATED TELESCOPIC FEMORAL NECK SCREW DEVICE AND RELATED FIXATION METHOD" and filed at the United States Patent and Trademark Office on Jan. 25, 2013.

FIELD

The present document generally relates to a screw assembly system and method for the fixation of fractures along the femoral neck, and in particular to an improved cannulated bone screw assembly that enables the implant to be used for the fixation of bone fractures through the physeal plate (growth plate).

BACKGROUND

Cannulated screws have been used for internal fracture fixation, and a single screw placement through the femoral neck has become the preferred treatment for fractures through the physeal plate. Fractures through the physeal plate are more commonly referred to as Slipped Capital Femoral Epiphysis.

Generally, such a fixation device comprises a hollow shaft having a predetermined cross-section and provided with threaded sections beginning at the medial end of the device spanning a predetermined length of the shaft. The fixation device is placed parallel to the neck of the femur and secures the fracture with compressive force applied by the spherical lateral screw head at the lateral cortex. The prior art typically describes a variety of screw systems comprising different shaft diameters, shaft lengths, thread pitches and thread lengths in order to offer a fixation device for all possible locations and extents of the fracture sites. The general configuration of cannulated screws is well illustrated in U.S. Pat. No. 7,207,994. Such described screws are non self-adjustable in length and, therefore incapable of providing a surgical fixation to stabilize fractured bones during the healing process without disrupting the normal bone growth particularly in pediatric patients.

In another example described in U.S. Published Patent Application No. 20070260248, an adjustable feature is incorporated into the screw allowing extension of the shaft length along a predetermined range. The screw has an outer member and an inner member connected together by a spring-like component. Once the shaft length is selected and the device is stabilized in said position, the device is inserted into the prepared canal of the femoral neck to fixate the bone segments, just as previously described for cannulated screws, in order to promote healing.

Other prior art include an intramedullary nail described as an adjustable solution for long bone fixation in U.S. Pat. No. 6,524,313. However, no prior art device has shown adjustable screw solutions for this regard. Therefore, there is a need in the art for an extendable screw system for surgical fixation of femoral neck fractures in pediatric patients.

Given the present design of cannulated screws used for the fixation of femoral neck fractures, including Slipped Capital Femoral Epiphysis, the compressive loads created by the medially threaded shafts and the lateral spherical screw heads inhibit the normal growth in young patients. Premature closure of the physeal plate is a reoccurring condition widely documented in the literature as a result of pinning and fixation via cannulated screws. Telescoping devices such as the Fassier-Duval Intramedullary Nail, whose fixation features do not thread into the physeal plate, have shown successful internal fixation of fractures and osteotomies in long bones without compromising the integrity of the physeal plate and thus allowing the continuation of normal patient growth.

SUMMARY

In one aspect, a cannulated screw assembly is provided that is self-extendable in length for surgical fixation of fractured femoral necks or slipped femoral epiphysis in a young patient.

In another aspect, a cannulated screw assembly is provided which requires minimally invasive instrumentation and a relatively straightforward surgical technique.

Hence, in accordance with one aspect of the screw assembly, a screw assembly for fixation of femoral neck fractures may include a telescopic assembly having two opposed ends and including a male component and a female component. The interconnected components permit axial movement of each end relative to each other. Anchorage of the female and male components is achieved through screw-type fixation of each end of the telescoping screw to the lateral cortex of the femur and the head of the femur. The smooth shaft design and lack of compression element allow free longitudinal extension of the length of the screw so that the screw is extendable as the bone heals and normal patient growth occurs.

According to one embodiment of the screw assembly with a beveled head design, the screw assembly is provided with an elongated tube having one end formed with an external self-tapping thread that has a diameter greater than the external diameter of the tube, and a cannulated rod having one end formed with an external self-tapping thread as large as the external diameter of the tube. The cannulated rod is adapted for insertion through a drilled canal into the bone until the self-tapping end is anchored in the medial end of bone (the epiphysis of the femoral head) and the rod spans the fracture site. The elongated tube is adapted for insertion into the bone, over the cannulated rod, until the external fixation thread at the lateral end of the tube is anchored within the lateral cortex of the bone. The screw assembly creates a stable fixation and inhibits radial displacements of the fractured segments of the bone while permitting longitudinal extendibility as the bone structures heals and normal patient growth occurs.

This embodiment of the screw assembly provides a relatively easy method of implantation because anchorage of the screw assembly is as would be anchorage of a single cannulated screw, wherein the action is achieved through rotating the respective rod and tube components until the threads anchor in the bone structures with the use of detachable driving tools. The position of the screw assembly is final when beveled head is parallel to surface of the lateral cortex.

According to another embodiment with a triblobe design, the screw assembly is provided with a male component with an elongated rod having one end formed with an external self-tapping thread that has a diameter greater than the external diameter of the tube, and a female component having one end formed with an external self-tapping thread that is the same diameter as the tube. The female component is adapted to be inserted through a drilled canal into the bone until the self-tapping end is anchored in the medial end of bone (the epiphysis of the femoral head) and the rod spans the fracture site. The male component is adapted to be inserted into the bone, inside the female component, until the external fixation thread at the lateral end of the rod is anchored within the lateral cortex of the bone.

An additional characteristic of this embodiment is to provide a cannulated screw assembly for surgical fixation of fractures bones which prevents rotational instability of the femoral epiphysis by preventing the rotation of the male and female components along the central axis. Rotation is hindered by interlocking of a non-circular feature (e.g. one or more flat surfaces, trilobe, cloverleaf, etc.) on the outer surface of the male component and the inner surface of the female component. The male component must be placed into the female component according to the specific mating pattern dictated by the interlocking feature on the components of the assembly. The screw assembly inhibits both radial displacements of the fractured segments of the bone and axial rotation of the segments around the axis of the screw assembly, while permitting longitudinal extendibility as the bone structures heal and normal patient growth occurs.

Moreover, the screw assembly provides a relatively easy method of implantation because the design allows anchorage of the screw assembly as would the anchorage of a single cannulated screw. The male and female components are assembled as per presented in the embodiment in order to screw in simultaneously both medial and lateral threading through a simple continuous rotation action with the use of a driving tool detachably connected to the male component, which in turn serves as the driving tool for the female component. Device position is final when all threads on tube have fully tapped into bone beyond the physeal plate within the femoral epiphysis.

In all embodiments, the screw assembly has a unique feature of self-adjustment in length after its implantation to provide a stable fixation of the fractured bone segments without the use of compressive forces to promote healing without disrupting normal patient growth, which is particularly advantageous when the screw assembly is used in children. In addition, rotational stability can be achieved by the incorporation of a non-circular design feature to block rotation between male and female components. Furthermore, retrieval features incorporated into the lateral ends of the embodiments of the present invention allow retention of the screws during insertion and removal procedures. Finally, a cap-like component completes the screw assembly, which inserts into the proximal end of the screw assembly at the lateral cortex in order to prevent bone in-growth for eased retrieval of the screw assembly once the fracture site is healed or patient growth is complete.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 16A is a cross-sectional view of the male component along line 16A-16A of FIG. 16;
FIG. 17 is a side view of the male component shown in FIG. 10;
FIG. 18 is a perspective of a third embodiment of the screw assembly having a beveled head configuration;
FIG. 22 is a perspective view of the female component shown in FIG. 18;
FIG. 22A is a cross-sectional view taken along line 22A-22A of FIG. 22;
FIG. 23 is a side view of the female component shown in FIG. 18;
FIG. 24 is a perspective view of the male component shown in FIG. 18;
FIG. 24A is a cross-sectional view taken along line 24A-24A of FIG. 24;
and
FIG. 25 is a side view of the male component shown in FIG. 18;
FIGS. 26A-26G illustrate one method for using the screw assembly shown in FIG. 1.

Corresponding reference characters indicate corresponding elements among the view of the drawings. The headings used in the figures should not be interpreted to limit the scope of the claims.

DETAILED DESCRIPTION

Figure 1:
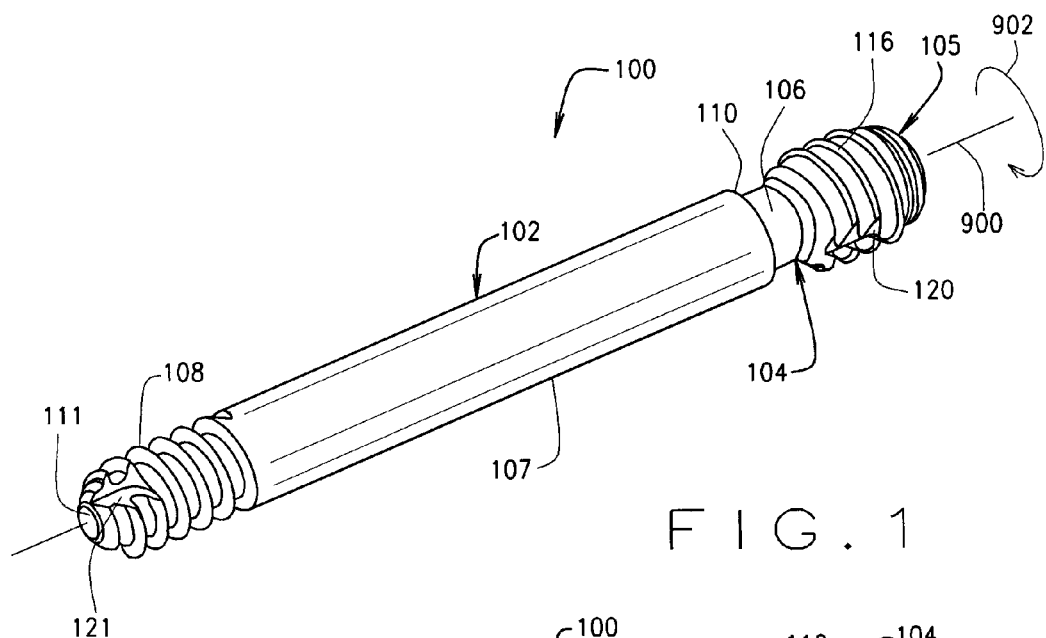
FIG. 1 is a perspective view of a first embodiment of a screw assembly having a trilobe configuration.

Referring to the drawings, various embodiments of the screw assembly are illustrated and generally indicated as 100, 200 and 300 in FIGS. 1-25.

In one embodiment shown in FIGS. 1-9, the screw assembly, designated 100, may include a hollow female component 102 configured to receive a male component 104 with a cap 105 that engages one end of the male component 104. Specifically, the male component 104 is freely slidable relative to female component 102 along longitudinal axis 900 (FIG. 1), which allows the screw assembly 100 to lengthen over time along axis 900 and accommodate the natural growth of the growth plate as the fracture heals over a period of time.

Figure 4:
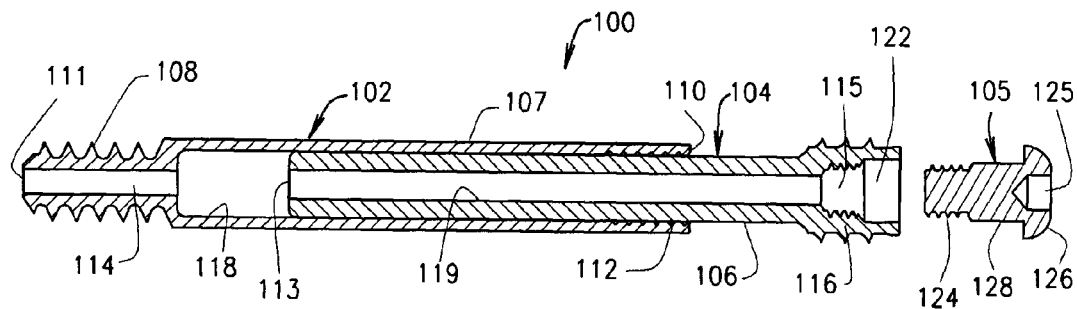
FIG. 4 is partially exploded side view of the screw assembly with the male component, female component, and cap.

Referring to FIGS. 1 and 4, the female component 102 defines circular-shaped hollow shaft 107 that defines an elongated trilobe-shaped channel 118 therein configured to accommodate a trilobe-shaped shaft 106 of the male component 104 such that the trilobe-shaped shaft 106 of the male component 104 may freely slide relative to the elongated trilobe-shaped channel 118 of the female component 102.

Figure 5:
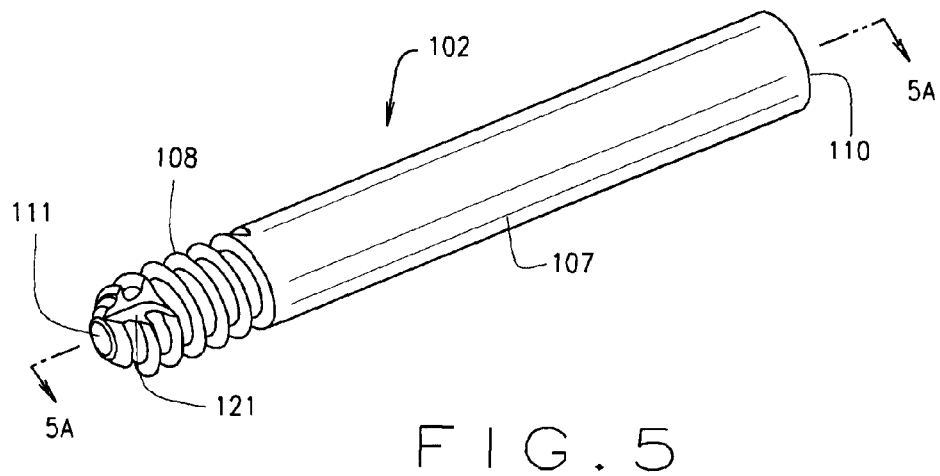
FIG. 5 is a perspective view of the female component.
Figure 5A:
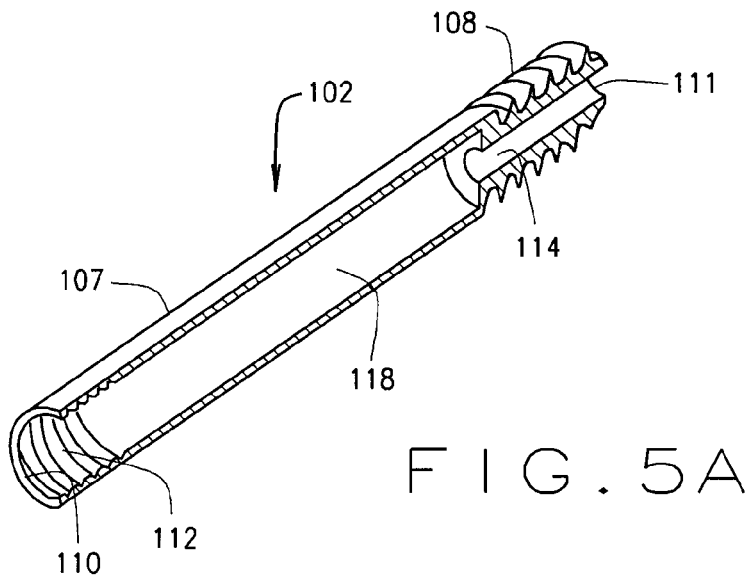
FIG. 5A is a cross-sectional view along line 5A-5A of FIG. 5.

Referring to FIGS. 5 and 5A, the circular-shaped hollow shaft 107 of the female component 102 further defines a proximal end opening 110 in communication with the elongated trilobe-shaped channel 118. In addition, the female component 102 further include a medial threaded portion 108, having a cancellous profile, that defines an axial opening 111 in communication with an interior cannulated section 114. The other end of the interior cannulated section 114 is in communication with the far end of the elongated trilobe-shaped channel 118 such that fluid flow communication is established between the axial opening 111 and the proximal end opening 110. In one embodiment, the inner diameter of the cannulated section 114 is less than the inner diameter of the elongated trilobe-shaped channel 118. As shown, one embodiment of the medial threaded portion 108 may define a self-tapping cut-out feature 121 that facilitates entry of the female component 102 into the bone as shall be described in greater detail below. As further shown, an internal threaded portion 112 is defined adjacent to the proximal end opening 110 for engaging with a removal device (not shown) with matching thread.

Figure 7:
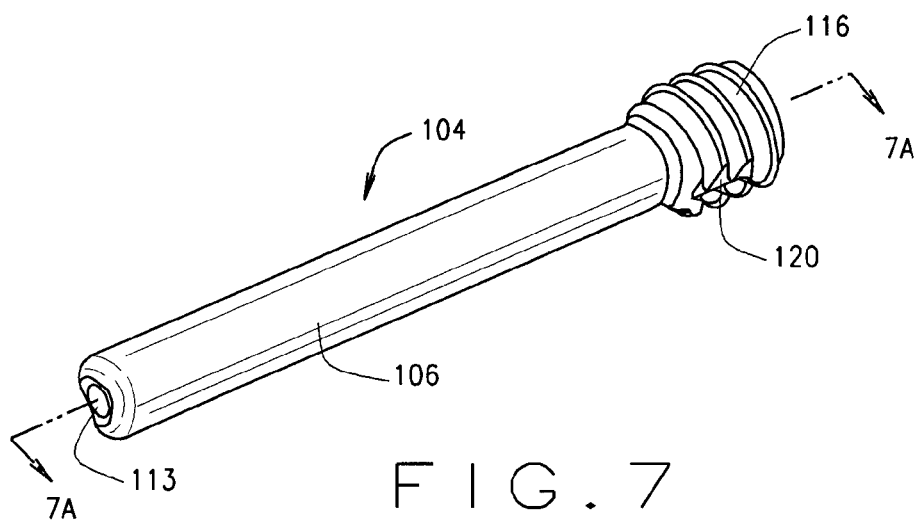
FIG. 7 is a perspective view of the male component
Figure 7A:
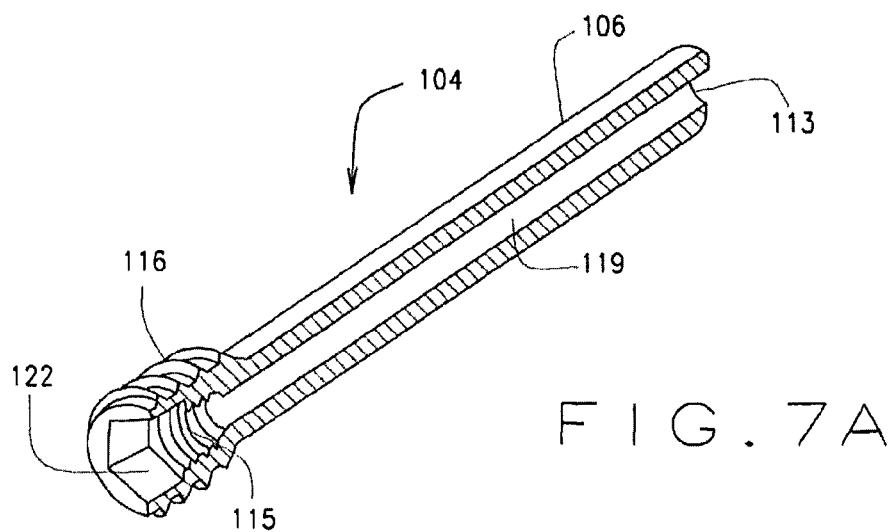
FIG. 7A is a cross-sectional view along line 7A-7A of FIG. 7.
Figure 8:
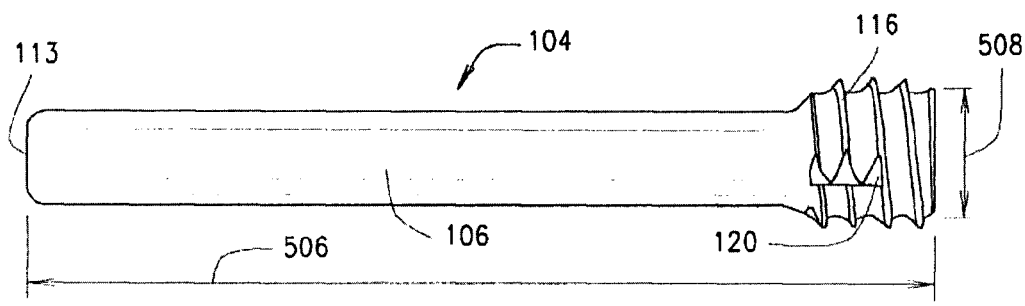
FIG. 8 is a side view of the male component.

As shown in FIGS. 7, 7A and 8, the male component 104 includes a trilobe-shaped shaft 106 having a substantially three-sided cross-sectional configuration sized and shaped to be disposed within the elongated trilobe-shaped channel 118 when the male component 104 is engaged to the female component 102. The male component 104 defines a far end opening 113 along a trilobe-shaped end 136 of the elongated trilobe-shaped shaft 106 and a lateral threaded portion 116 at the opposite end of the elongated trilobe-shaped shaft 106. The lateral threaded portion 116 features a flat head configuration at the free end thereof that positions the lateral threaded portion 116, whose diameter is larger than the trilobe-shaped shaft 106. In addition, the lateral threaded portion 116 defines a self-tapping feature 120 formed along the lateral threaded portion 116.

As shown in FIG. 7A, the far end opening 113 is in communication with a cannulated section 119 which forms a channel along the length of the elongated trilobe-shaped shaft 106. In addition, a drive feature 122 communicates with the opposite end of the cannulate section 119 through an internal threaded section 115 formed adjacent the drive feature 122, whose combination is used to retain and drive the assembled male and female components simultaneously into the bone (FIG. 26A).

Figure 2:
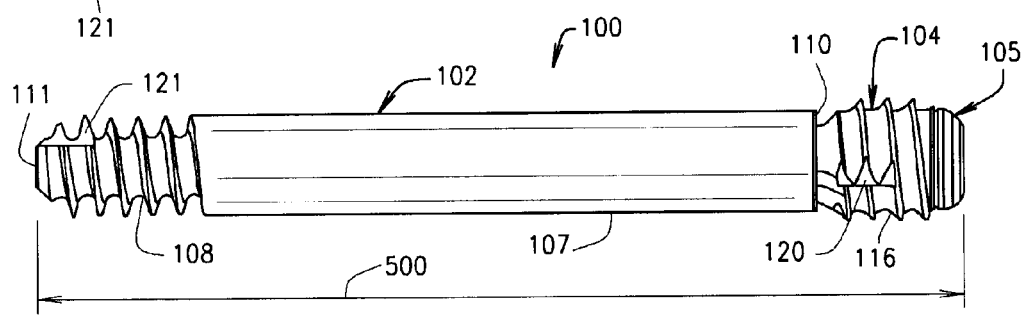
FIG. 2 is a side view of the screw assembly.
Figure 3:
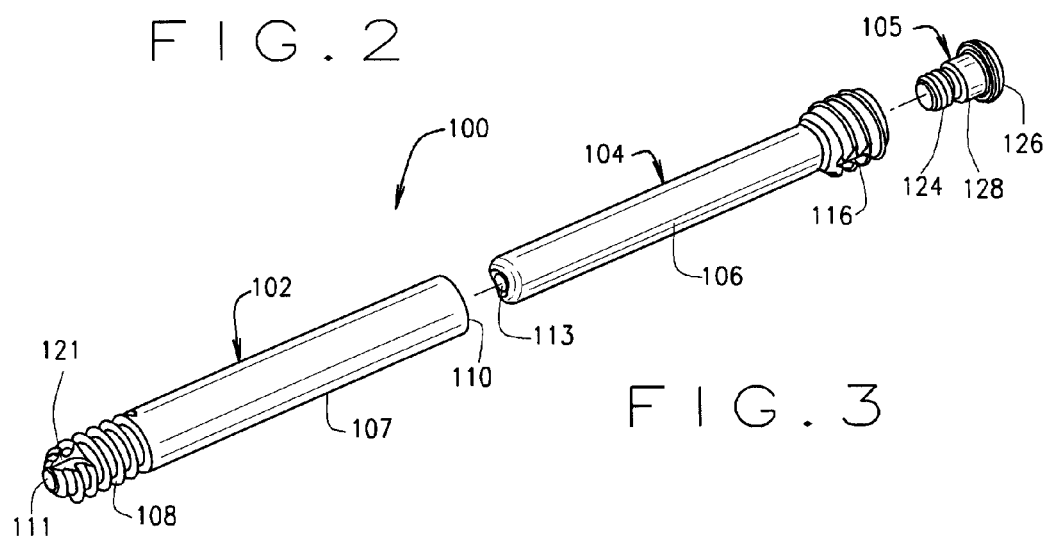
FIG. 3 is an exploded view of the screw assembly showing the female component, male component and cap.
Figure 3A:
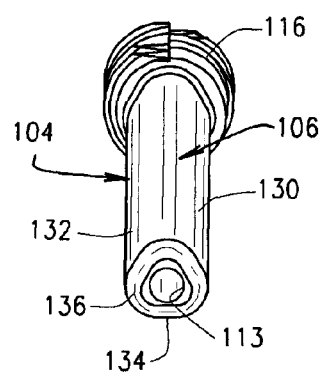
FIG. 3A is an end view of the male component.

Referring to FIG. 3A, the trilobe-shaped shaft 106 includes a first trilobe portion 130, a second trilobe portion 132, and a third trilobe portion 134 that collectively form a non-cylindrical cross-sectional configuration that prevents rotation of the female component 102 relative to the male component 104. As noted above, the trilobe-shaped shaped shaft 106 is freely slidable along longitudinal axis 900 of the screw assembly 100, while the non-circular shape of the trilobe-shaped shaft 106 prevents rotational movement of the female component 102 relative to the male component 104 along rotational direction 902 (e.g. in either the clockwise or counter-clockwise rotational directions). Although the embodiment of the male component 104 shown in FIGS. 1-8 defines a three-sided trilobe-shaped cross-sectional configuration, other types of non-cylindrical cross-sectional configurations may be used to define the shaft 106, such as triangular, square, rectangular, or oblong-shaped cross-sectional configurations that allows sliding movement of the male component 104, but prevents rotational movement of the female component 102 relative to the male component 104. In this mating engagement between the female component 102 and the male component 104, the drive mechanism 10 is able to drive both female and male components 102 and 104 into the bone.

Figure 9A:
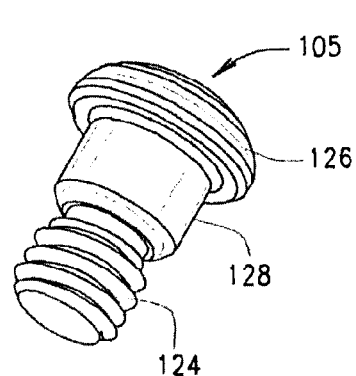
FIGS. 9A and 9B are perspective views of the cap.
Figure 9B:
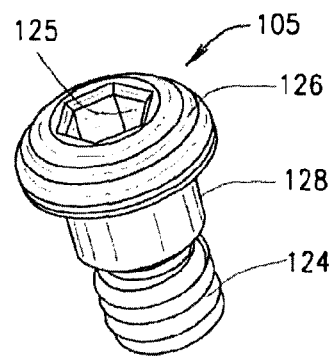
Figure 10:
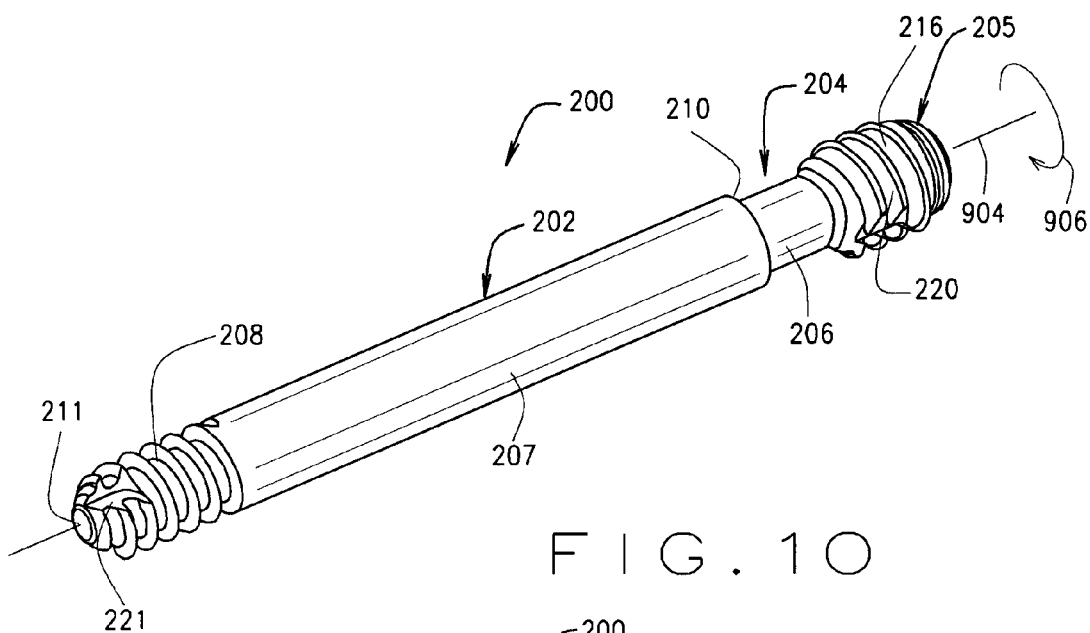
FIG. 10 is a perspective view of a second embodiment of the screw assembly having a double flat configuration.

Referring to FIGS. 9A and 9B, the cap 105 may be used to seal off the recessed drive feature 122 of the male component 104. As shown, the cap 105 includes a semi-spherical shaped cap portion 126 that defines a recess 125 configured to connect with a drive and removal tool 11 with a matching profile. The cap portion 126 communicates with a cylindrical-shaped middle portion 128 with an external threaded portion 124 that extends axially from the middle portion 128. As shown in FIG. 4, the external threaded portion 124 of the cap 105 is configured to engage and retain the proximal end internal threads 115 defined by the male component 104.

Figure 6:
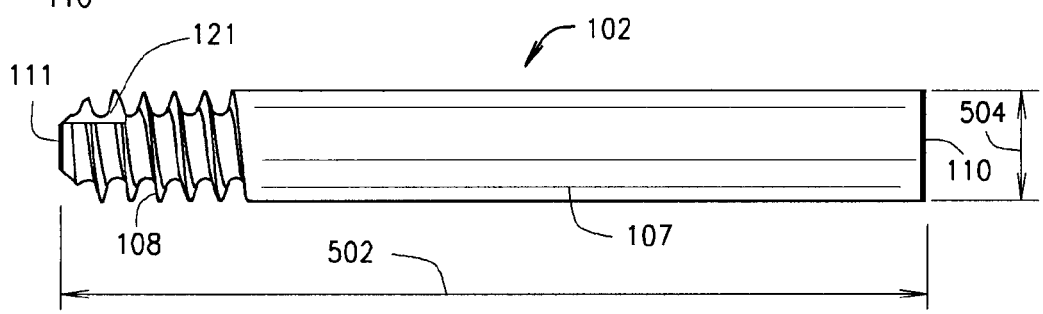
FIG. 6 is a side view of the female component.

During manufacture, the following dimensions may be used for one embodiment of the screw assembly 100, although other suitable dimensions may be used for other embodiments. Referring to FIGS. 2 and 6, the screw assembly 100 may have a length 500 of between 60 mm to 102 mm in 2 mm increments, while the female component 102 may have a length 502 of between 52 mm to 92 mm in 4 mm increments and a width 504 of 6.5 mm to 7.3 mm. As shown in FIG. 8, the male component 104 may have a length 506 of between 48 mm to 50 mm and a width 508 at the head 508 of between 8.0 mm to 9.0 mm.

Figure 11:
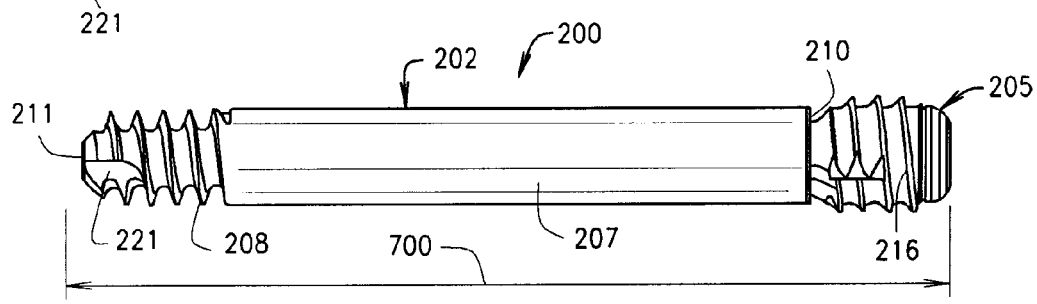
FIG. 11 is a side view of the screw assembly shown in FIG. 10.
Figure 12:
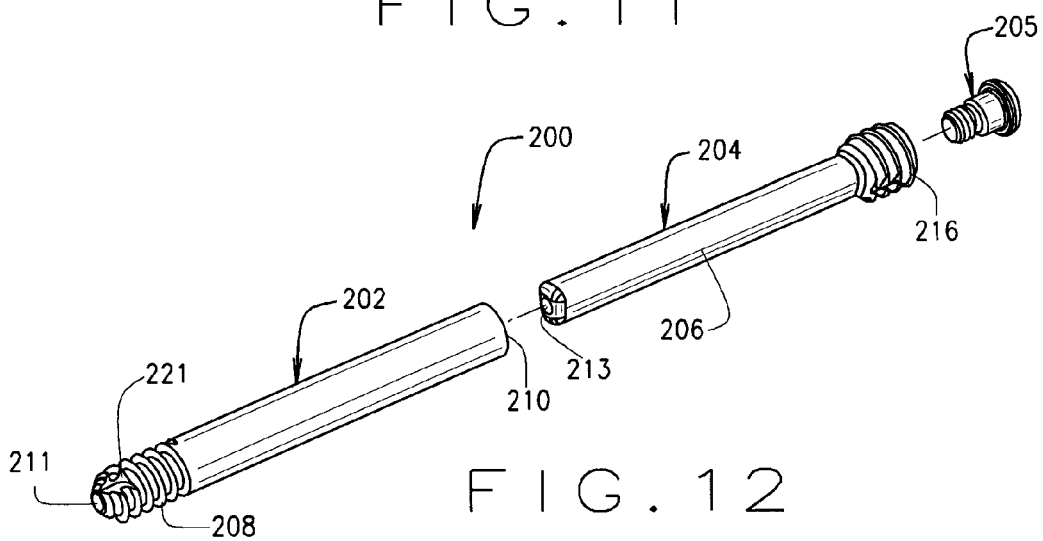
FIG. 12 is an exploded view of the screw assembly shown in FIG. 10 illustrating the female component, male component and cap.
Figure 12A:
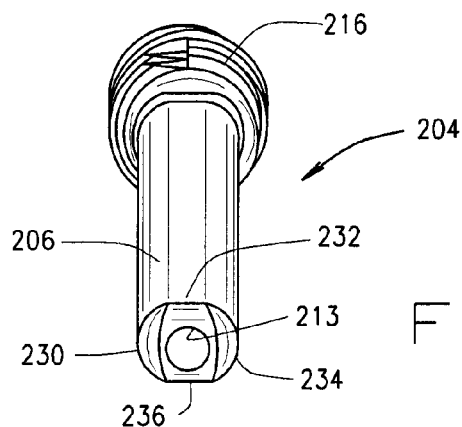
FIG. 12A is an end view of the male component shown in FIG. 12.

In a second embodiment shown in FIGS. 10-17, the screw assembly, designated 200, may include a hollow female component 202 configured to receive a male component 204 with a cap 205 that engages the male component 204 in similar fashion as cap 105. As shown in FIG. 12A, the male component 204 includes a double flat shaped shaft 206 having opposing sides 232 and 236 as well as opposing sides 230 and 234 that collectively define either a generally squared-shaped or rectangular-shaped cross sectional configuration. Similar to screw assembly 100, the non-cylindrical shape of the double flat shaped shaft 206 for the male component 204 functions in a similar manner as the trilobe-shaped shaft 106 of male component 104 to prevent rotational movement 906 of the female component 202 relative to the male component 204 while allowing free sliding movement along longitudinal axis 904 of the screw assembly 200.

Figure 14:
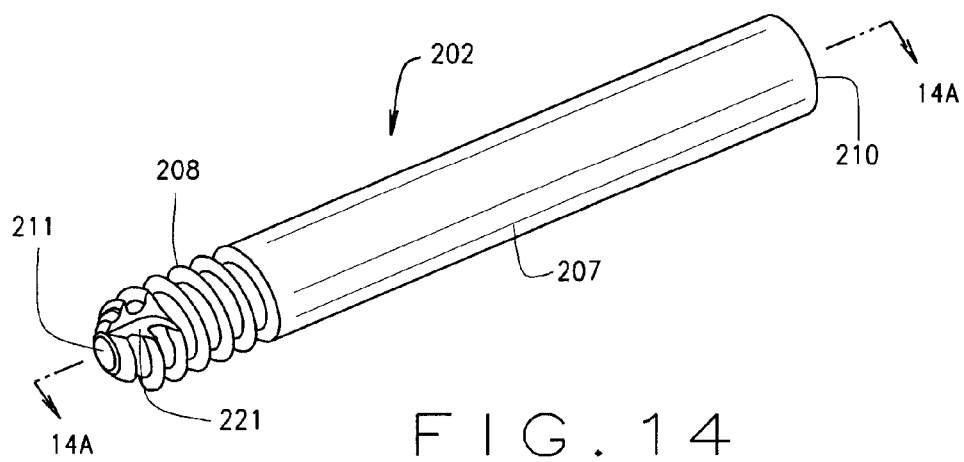
FIG. 14 is a perspective view of the female component shown in FIG. 10.
Figure 14A:
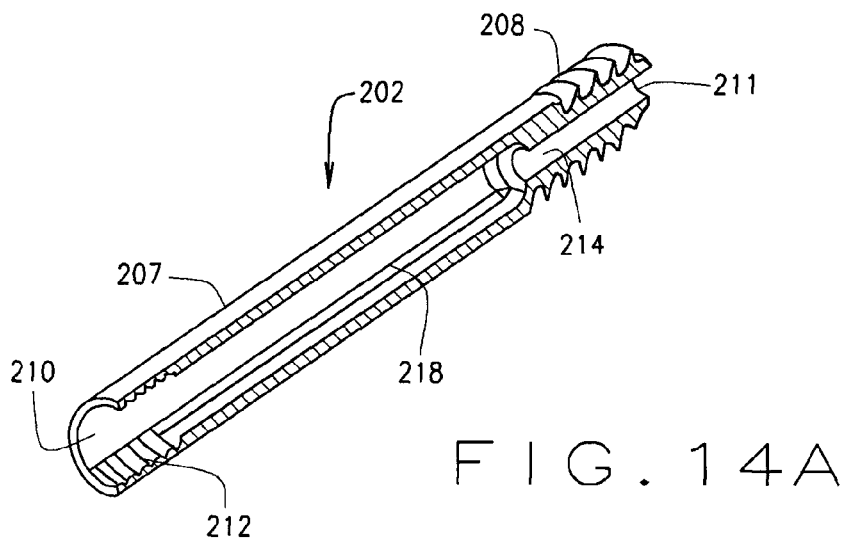
FIG. 14A is a cross-sectional view taken along line 14A-14A of FIG. 14.
Figure 15:
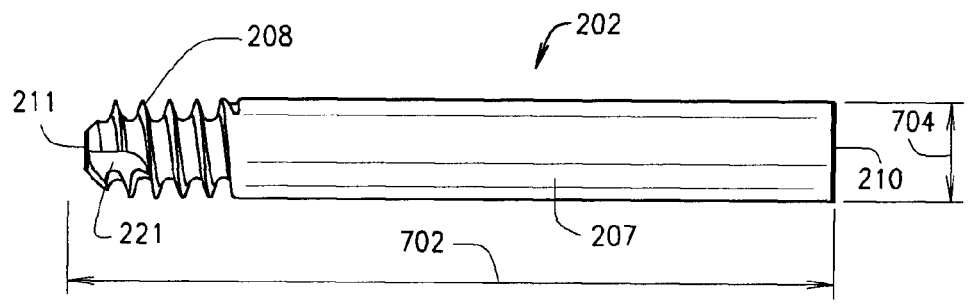
FIG. 15 is a side view of the female component shown in FIG. 10.
Figure 16:
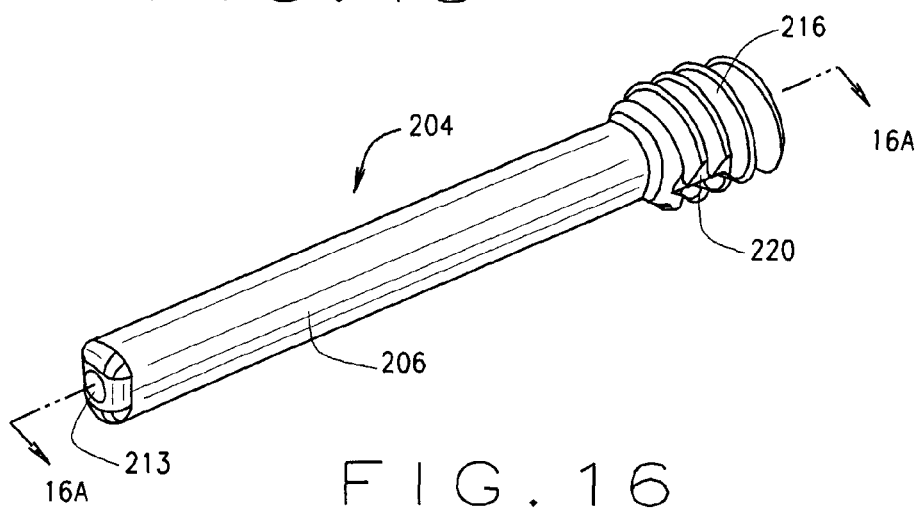
FIG. 16 is a perspective view of the male component shown in FIG. 10.

Referring to FIGS. 14 and 15, the female component 202 includes a cylindrically-shaped elongated hollow body 207 having a proximal end opening 210 at one end and an external threaded portion 208 at the opposite end thereof. In one embodiment, the external threaded portion 208 may have a cancellous-shaped profile having a diameter substantially equivalent to the diameter of the cylindrically-shaped elongated hollow body 207 for providing increased mechanical properties under weight bearing conditions. In addition, the external threaded portion 208 includes a self-tapping feature 221 that facilitates entry of the female component 102 into the bone and an axial opening 211.

Figure 13:
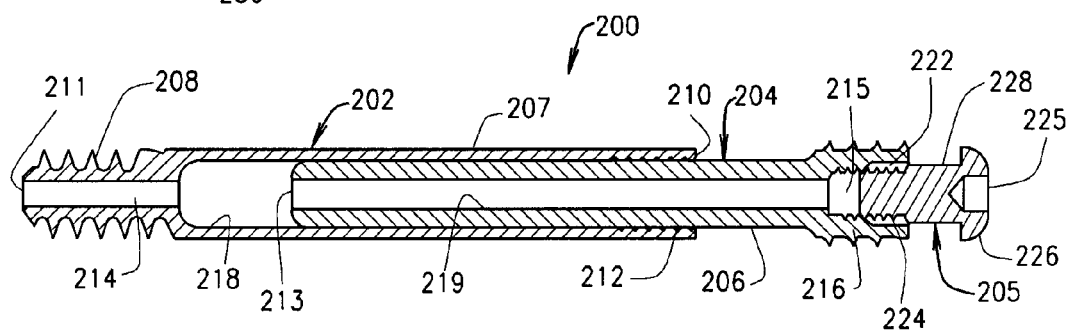
FIG. 13 is a partially exploded side view of the screw assembly shown in FIG. 10 with the male component, female component, and cap.

As shown in FIG. 13, the axial opening 211 is in communication with a cannulated section 214 formed through the external threaded portion 208 of the female component 202. In addition, the cannulated section 214 is in communication with an elongated channel 218 formed through the cylindrically-shaped elongated hollow body 207 that is configured to receive the male component 204 therein. In one embodiment, the elongated channel 218 defines a double-sided cross sectional configuration having the same cross sectional configuration as the double sided-shaped shaft 206. As further shown, a left handed internal threaded section 212 is formed proximate the proximal end opening 210 and is configured to mate with a removal instrument (not shown) for ease of retrieval of the female component 202.

Referring to FIGS. 13, 16, 16A and 17, the male component 204 defines a medial threaded portion 216 having a flat head with a self tapping feature 220 formed along the medial threaded portion 216. In one embodiment, a drive feature 222 forms a hexagonal-shaped recess in communication with a proximal end internal threaded portion 215 configured to engage an external threaded portion 224 of the cap 205 when the cap 205 is engaged into the male component 204. The combination of the drive feature 222 and the internal threaded portion 215 is used to retain and drive the assembled male and female components 202 and 204 into the bone (FIG. 26A). In addition, the male component 204 includes an axial opening 213 in communication with cannulated section 219 that forms an elongated channel between the axial opening and the drive feature 222. As shown, the cap 205 is similar in construction as cap 105 having a middle portion 228 in communication with a cap portion 226 having a recess 225.

During manufacture, the following dimensions may be used for one embodiment of the screw assembly 200, although other suitable dimensions may be used for other embodiments. Referring to FIG. 11, the screw assembly 200 may have a length 700 of between 60 mm to 102 mm in 2 mm increments. As shown in FIG. 15, the female component 202 may have a length 702 of between 50 mm to 90 mm in 4 mm increments and a width 704 of between 6.5 mm and 7.3 mm. As shown in FIG. 17, the male component 204 may have a length 706 of between 48 mm to 50 mm and a width 708 of between 8.0 mm to 9.0 mm In a third embodiment shown in FIGS. 18-25, the screw assembly, designated 300, may include a hollow female component 302 configured to receive a male component 304. As shown in FIGS. 22, 22A, and 23, the female component 302 defines a hollow cylindrical shaft portion 306 having a far end opening 310 formed at one end and a lateral beveled end portion 308 at the opposite end thereof. The hollow cylindrical shaft portion 306 allows for ease of insertion of the screw assembly 300 into the bone and eliminates disruption of the physeal plate as not sharp features are inserted into the physeal plate. The far end opening 310 is in communication with an elongated channel 320 formed along the cylindrical shaft portion 306.

As shown in FIG. 22A, an internal drive feature 322 is formed at the proximal end inside the lateral beveled end portion 308 and forms a hexagon-shaped recess. The drive feature 322 is configured to receive a portion of the drive mechanism 10 (FIG. 26A) for insertion through a bone. As further shown, a left-handed internal threaded portion 324 is formed between the drive feature 322 and a cannulated section 326. The left-handed internal threaded portion 324 facilitates retention of the screw assembly 300 for ease of removal, while the cannulated section 326 for guided insertion of the component into the bone using a cannulated rod (not shown). The lateral beveled end portion 308 has a diameter larger than the hollow shaft portion 306 for better retention of the screw assembly 300 in the bone.

Figure 19:
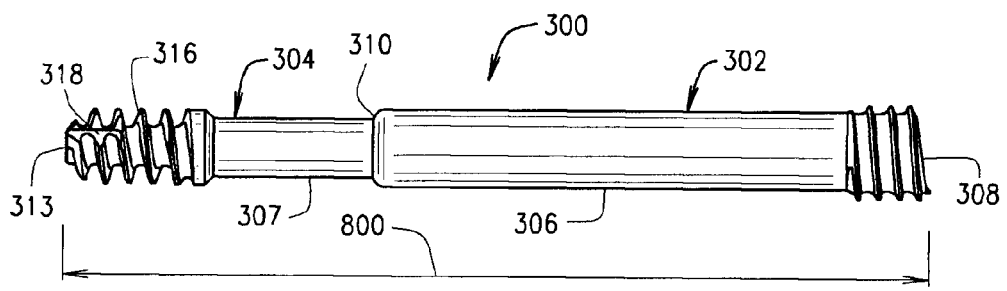
FIG. 19 is a side view of the screw assembly shown in FIG. 18.

Referring to FIG. 19, the lateral beveled end portion 308 defines a beveled profile that positions the cortical profiled threads of the lateral beveled end portion 308 fully within the lateral cortex, flush against the bone surface, thereby eliminating exposure of the threads outside the bone.

As shown in FIGS. 20, 24, 24A, and 25, the male component 304 defines a hollow cylindrical shaft portion 307 with a medial threaded portion 316 having a cancellous profile formed at one end of the shaft portion 307 and an external drive feature 312 formed at the opposite end thereof. The medial threaded portion 316 defines a self-tapping feature 318 that facilitates entry of the male component 304 into the bone. In some embodiments, the medial threaded portion 316 has a diameter larger than the diameter of the cylindrical shaft 307. As shown, an axial opening 313 is formed proximate the medial threaded portion 316 and is in communication with an elongated channel 325 at one end thereof. The external drive feature 312 forms an opening 315 that communicates with the opposite end of the elongated channel 325. As such, the male component 304 is fully cannulated to insert over a standard guide wire (not shown). In addition, the hollow cylindrical shaft portion 307 defines a left-handed retrieval threaded section 314 formed proximate the external drive feature 312.

Figure 20:
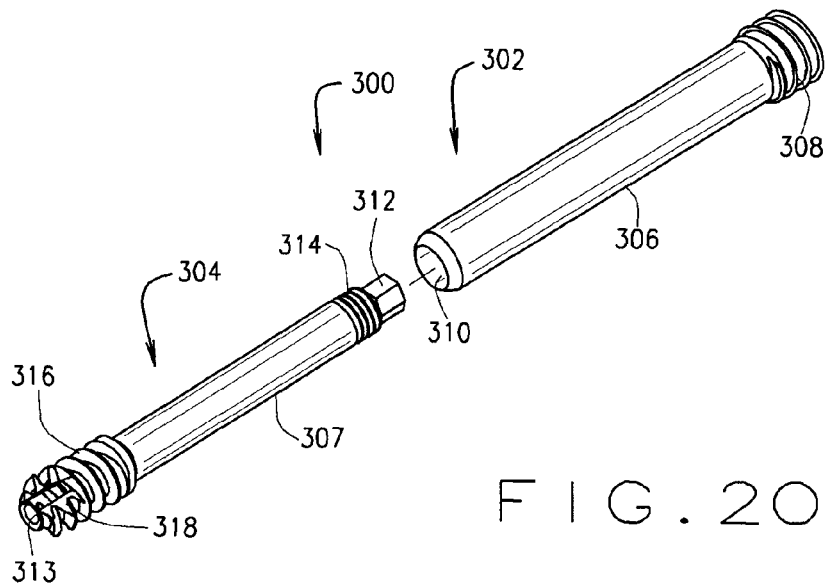
FIG. 20 is an exploded view of the screw assembly shown in FIG.
Figure 21:
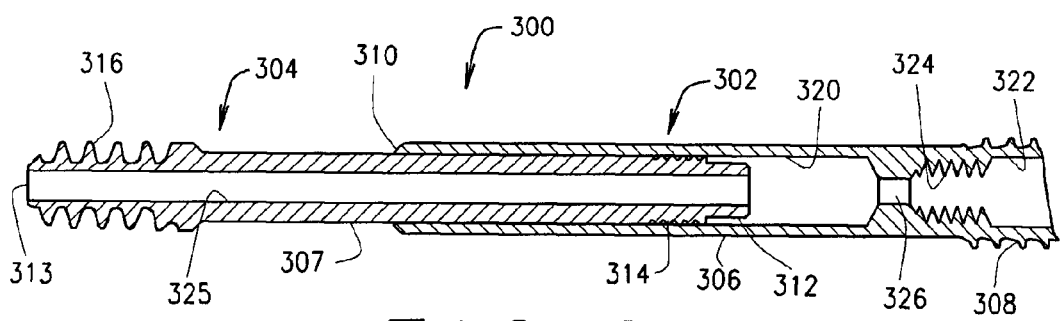
FIG. 21 is a partially exploded side view of the screw assembly shown in FIG. 18 with the male component and female component.

As shown in FIG. 20, the male component 304 may freely slide relative to the female component 302. In this embodiment, no cap is required to be engaged to the male component 304.

During manufacture, the following dimensions may be used for one embodiment of the screw assembly 300, although other suitable dimensions may be used for other embodiments. Referring to FIG. 19, the screw assembly 300 may have a length 800 of between 60 mm to 100 mm in 2 mm increments. As shown in FIG. 23, the female component 302 may have a length 802 of between 50 mm to 80 mm in 4 mm increments and a width 804 at the shaft of between 8.0 mm to 9.0 mm. As shown in FIG. 25, the male component 304 may have a length 806 of 50 mm, a width 808 at the shaft of between 5.0 mm and 5.8 mm and a width 808 at the head of between 6.5 mm to 7.3 mm.

Figure 26B:
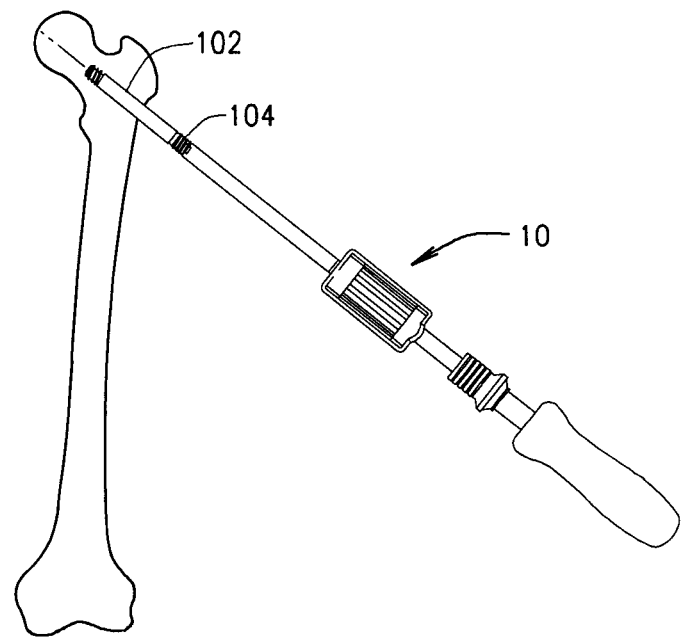
Figure 26C:
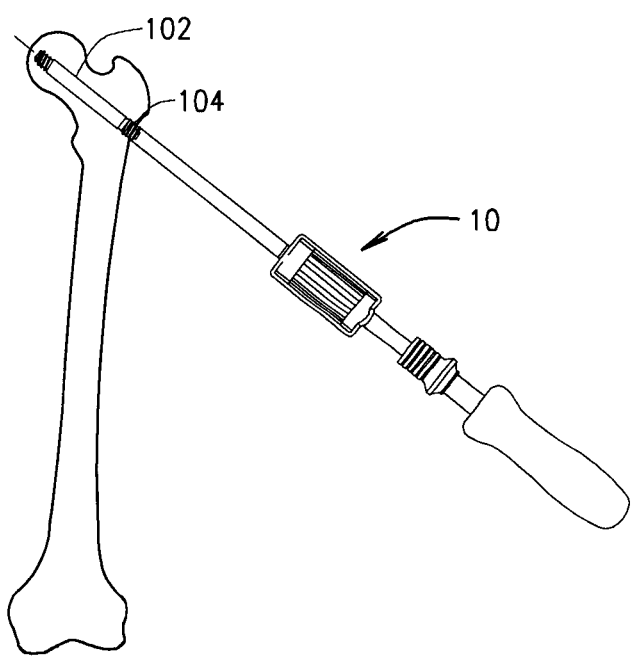
Figure 26D:
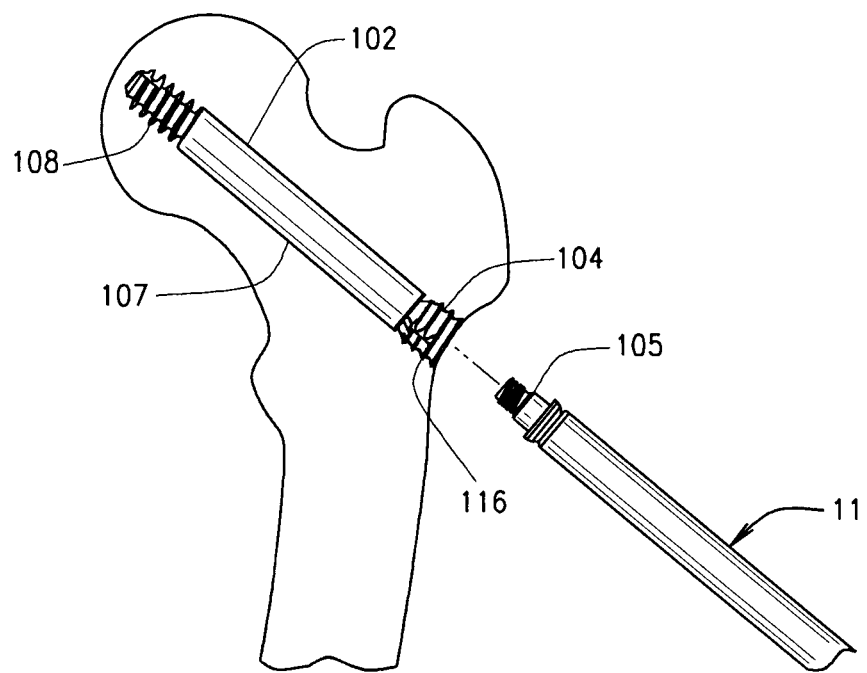
Figure 26E:
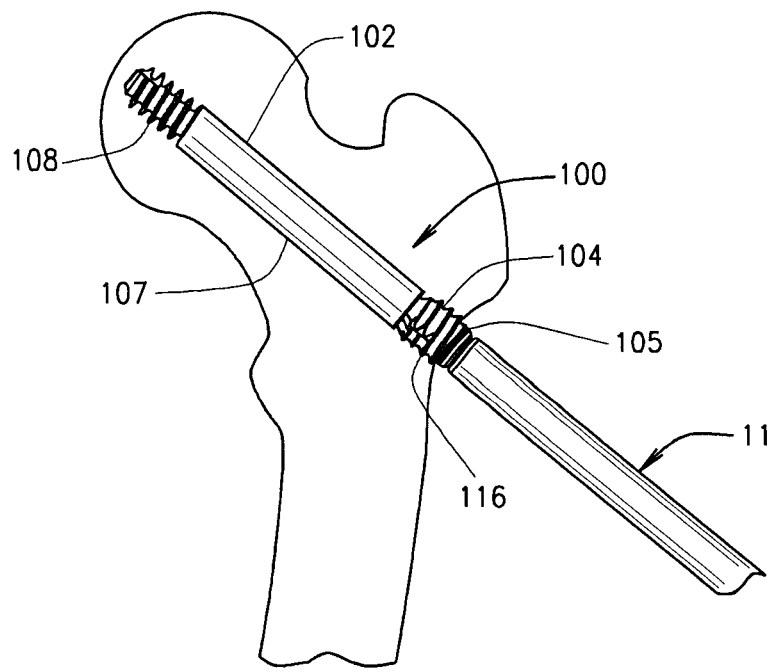
Figure 26F:
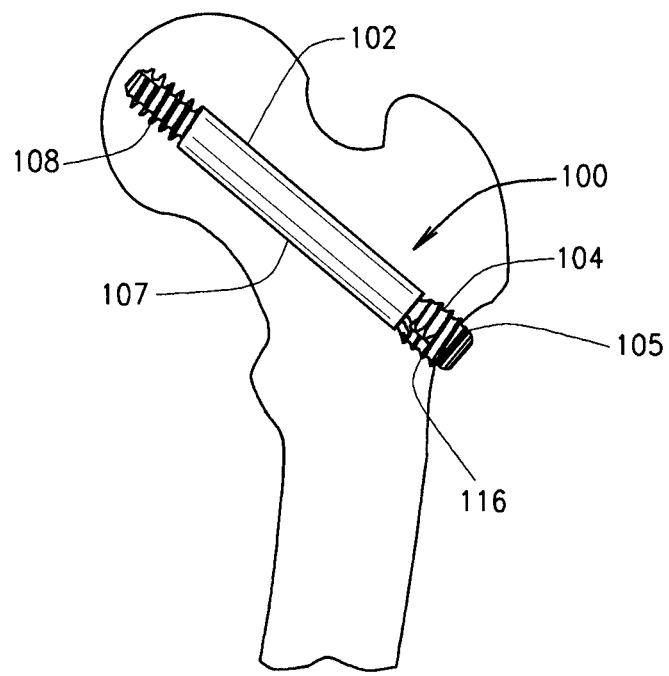
Figure 26G:
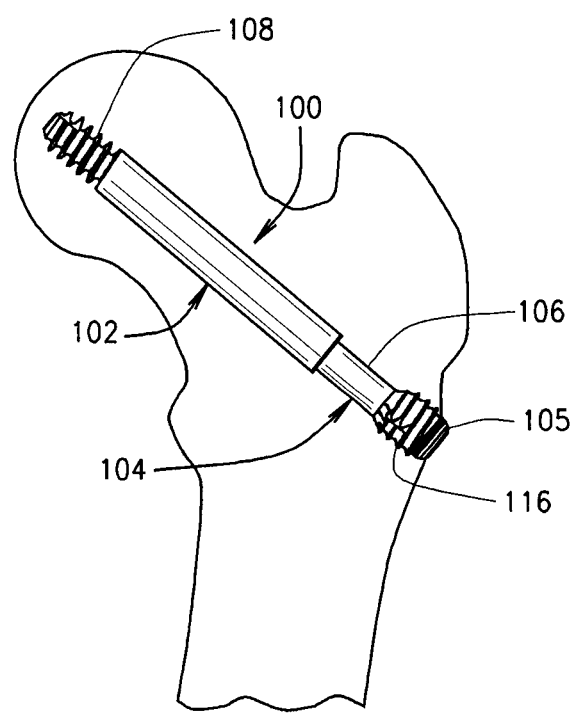

Referring to FIGS. 26A-26G, one method of using the screw assemblies 100 and 200 is illustrated. However, for ease of description only the use of screw assembly 100 will be described herein since the method of use is the same for both embodiments. Referring to FIGS. 26A-26C, the male component 104 received within the female component 102 is inserted through the physeal plate using a drive mechanism 10 until the lateral threaded portion 116 of the male component 104 is fully disposed within the lateral cortex. In this arrangement, the male component 104 is fully received within the female component 102 such that the cylindrical shaft 106 is fully disposed within the female component 102. As shown in FIGS. 26D-26F, the cap 105 is attached to the lateral threaded portion 116 using the driving mechanism 11 which seals off both the male component 104 and female component 102 within the lateral cortex. As shown in FIG. 26G, the free sliding engagement between the female component 102 and the male component 104 allows the cylindrical shaft 106 to gradually extend from the female component 102 as the physeal plate grows over time as the fracture heals.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method for fixation and healing of a slipped capital femoral epiphysis (SCFE) or a neck fracture of a femur of a mammal, the femur having a physeal plate and a lateral cortex, the method comprising the steps of:
   a) providing a female component comprising:
      a hollow elongated shaft defining a medial threaded portion at one end of the hollow shaft and a lateral end opening at the opposite end thereof, wherein the lateral end opening is in communication with a non-cylindrically shaped channel formed along the hollow shaft, the medial threaded portion being adapted to be fixed into an inner side of a femoral neck through the physeal plate;
   b) providing a male component comprising:
      a non-cylindrical shaped shaft adapted to be slidably inserted within the non-cylindrically shaped channel of the female component, and
      a lateral threaded portion at one end of the non-cylindrical shaped shaft, the lateral threaded portion abutting the lateral opening of the female component when the male component is fully received within the female component, the lateral threaded portion being adapted to engage the lateral cortex of the femur;
   wherein the non-cylindrical shaped channel of the female component defines substantially the same cross-sectional configuration as the non-cylindrical shaped shaft of the male component such that the male component is freely slidable relative to the female component along a longitudinal axis defined by the screw assembly; and wherein the non-cylindrical shape of the channel of the female component and of the shaft of the male component avoid rotation of the male component relative to the female component;
   c) inserting the male component into the female component until the male component is fully received within the female component to form an extendable screw assembly; and
   d) screwing the extendable screw assembly through the physeal plate in a way that the medial threaded portion of the female component engages the inner side of the femoral neck and until the lateral threaded portion of the male component is also fully engaged within the lateral cortex of the femur;
   wherein once the extendable screw assembly has been entirely screwed within the femur, the non-rotational free sliding engagement between the female component and the male component allows the extendable screw assembly to gradually extend as the physeal plate grows over time as the fracture or the SCFE heals.

2. The method as claimed in claim 1, wherein the extendable screw assembly further comprises a cap configured to engage a recessed drive feature of the male component once the extendable screw assembly is screwed within the femoral neck; the recessed drive feature being located at said one end of the non-cylindrical shaped shaft, the recessed drive feature being adapted for receiving a drive mechanism for screwing the extendable screw assembly within the femoral neck until the medial threaded portion and the lateral threaded portion are both screwed inside the femoral neck and lateral cortex respectively, the method further comprising the step of:
   sealing off the recessed drive feature of the male component by engaging and attaching the cap using a secondary drive mechanism.

3. The method as claimed in claim 2, wherein the recessed drive feature of the male component forms a hexagonal-shaped recess proximate to the lateral threaded portion.

4. The method as claimed in claim 3, wherein the male component defines a second lateral threaded portion formed proximate the recessed drive feature, wherein the second lateral threaded portion is configured to engage the cap and the drive mechanism.

5. The method as claimed in claim 2, wherein the cap comprises a middle portion with a cap portion formed at one end of the middle portion and an external threaded portion formed at the opposite end thereof.

6. The method as claimed in claim 2, wherein the extendable screw assembly further comprises the drive mechanism configured to engage the recessed drive feature of the screw assembly for inserting the screw assembly into the femur.

7. The method as claimed in claim 1, wherein the non-cylindrical shaped shaft of the male component and the non-cylindrical shaped channel of the female component each have a three sided cross sectional configuration or a double flat cross-sectional configuration.

8. The method as claimed in claim 1, wherein the non-cylindrical shaped shaft of the male component and the non-cylindrical shaped channel of the female component each have a triangular, square, rectangular, or oblong cross-sectional configurations.

9. The method as claimed in claim 1, wherein the lateral threaded portion of the male component defines a cortical-shaped profile.

10. The method as claimed in claim 1, wherein the medial threaded portion of the female component defines a cancellous-shaped profile.

11. The method as claimed in claim 1, wherein the medial threaded portion of the female component includes a self-tapping feature defining a flat surface area.

12. The method as claimed in claim 1, wherein a diameter of the medial threaded portion is as large as an external diameter of the hollow elongated shaft.

13. The method as claimed in claim 1, wherein the lateral threaded portion of the male component includes a self-tapping feature that defines a flat surface area.

14. The method as claimed in claim 1, wherein the medial threaded portion of the female component defines an axial opening in communication with the non-cylindrical shaped channel.

15. The method as claimed in claim 1, wherein the extendable screw assembly further comprises a left handed internal threaded section formed proximate the lateral end opening of the female component and configured to mate with a removal instrument for ease of retrieval of the female component from the femur.

16. The method as claimed in claim 1, wherein the mammal is a skeletally immature human.

* * * * *